(12) United States Patent
Greaves

(10) Patent No.: US 10,596,093 B2
(45) Date of Patent: Mar. 24, 2020

(54) COSMETIC USE AS DEODORANT ACTIVE AGENT OF A SILICEOUS MATERIAL OBTAINED BY HYDROLYSIS AND CONDENSATION OF A TETRAALKOXYSILANE AND OF A $C_7$-$C_{20}$-ALKYLTRIALKOXYSILANE

(71) Applicant: L'OREAL, Paris (FR)

(72) Inventor: Andrew Greaves, Magny-le-Hongre (FR)

(73) Assignee: L'OREAL, Paris (FR)

( * ) Notice: Subject to any disclaimer, the term of this patent is extended or adjusted under 35 U.S.C. 154(b) by 98 days.

(21) Appl. No.: 14/893,564

(22) PCT Filed: May 16, 2014

(86) PCT No.: PCT/EP2014/060080
§ 371 (c)(1),
(2) Date: Nov. 24, 2015

(87) PCT Pub. No.: WO2014/191236
PCT Pub. Date: Dec. 4, 2014

(65) Prior Publication Data
US 2016/0143832 A1    May 26, 2016

(30) Foreign Application Priority Data
May 30, 2013 (FR) ...................................... 13 54908

(51) Int. Cl.
*A61K 8/58* (2006.01)
*A61Q 15/00* (2006.01)

(52) U.S. Cl.
CPC .............. *A61K 8/585* (2013.01); *A61Q 15/00* (2013.01); *A61K 2800/40* (2013.01)

(58) Field of Classification Search
None
See application file for complete search history.

(56) References Cited

U.S. PATENT DOCUMENTS

| 4,017,528 A * | 4/1977 | Unger ..................... C08G 77/02 502/150 |
| 5,185,169 A * | 2/1993 | Yamamoto .............. A61L 9/046 427/246 |

* cited by examiner

*Primary Examiner* — Bethany P Barham
*Assistant Examiner* — Barbara S Frazier
(74) *Attorney, Agent, or Firm* — Polsinelli PC

(57) ABSTRACT

The invention thus relates to the cosmetic use of a siliceous material that may be obtained by hydrolysis and condensation, in the presence of water, of at least one tetraalkoxysilane of formula (I) below: Si(OR2)4 (I) and of an alkyltrialkoxysilane of formula (II) below: $R_1Si(OR_2)_3$ (II) in which: $R_1$ denotes a $C_7$ to $C_{20}$ alkyl group, optionally interrupted in its chain with an O or S atom or with an NH group or a carbonyl group (CO), $R_2$ denotes a $C_1$-$C_4$ alkyl group. Preferentially, the siliceous material is present in a composition comprising a cosmetically acceptable medium. The invention also relates to a cosmetic process for treating human body odour, in particular underarm odour and optionally human perspiration, which consists in applying to human keratin materials the said siliceous material or a composition containing the same in a cosmetically acceptable medium. The invention also relates to a composition characterized in that it comprises, in a cosmetically acceptable medium, at least the said siliceous material and at least one deodorant agent other than the said siliceous material and/or at least one antiperspirant active agent.

19 Claims, No Drawings

COSMETIC USE AS DEODORANT ACTIVE AGENT OF A SILICEOUS MATERIAL OBTAINED BY HYDROLYSIS AND CONDENSATION OF A TETRAALKOXYSILANE AND OF A $C_7$-$C_{20}$-ALKYLTRIALKOXYSILANE

CROSS REFERENCE TO RELATED APPLICATIONS

This application is a National Phase filing under 35 U.S.C. § 371 of PCT/EP2014/060080 filed on May 16, 2014; and this application claims priority to Application No. 1354908 filed in France on May 30, 2015 under 35 U.S.C. § 119. The entire contents of each application are hereby incorporated by reference.

The present invention relates to the cosmetic use as a deodorant active agent of a siliceous material that may be obtained by hydrolysis and condensation of at least one tetraalkoxysilane and of at least one $C_7$-$C_{20}$-alkyl trialkoxysilane; in particular, the said siliceous material is present in a composition comprising a cosmetically acceptable medium.

The invention also relates to a cosmetic process for treating human body odour, in particular underarm odour and optionally human perspiration, which consists in applying to human keratin materials the said siliceous material or a composition containing the same in a cosmetically acceptable medium.

The invention also relates to a composition characterized in that it comprises, in a cosmetically acceptable medium, at least the said siliceous material and at least one deodorant agent other than the said siliceous material and/or at least one antiperspirant active agent.

Eccrine or apocrine sweat has little odour when it is secreted. It is its degradation by bacteria via enzymatic reactions which produces malodorous compounds. The compounds which contribute to unpleasant underarm odour comprise malodorous steroids, volatile fatty acids, especially aliphatic, branched, saturated and/or unsaturated ($C_2$-$C_{12}$) fatty acids, and sulfanylalkanol compounds (Chem. Biodivers., 1, 1058-1072, (2004)). Certain precursors of odorous substances and mechanisms for generating them are described in the scientific literature [see, for example, Journal of Investigative Dermatology, 130, 529-540, (2010); Int. J. Cosmet. Sci., 26, 149-156, (2004)].

The function of deodorant active agents is to reduce or prevent the formation of unpleasant odours. The various systems proposed hitherto may be grouped mainly into four large families i) to iv).

i) Bactericidal substances or substances which limit the growth of bacteria. Bactericides destroy the resident bacterial flora. The most widely used bactericides are triclosan (2,4,4'-trichloro-2'-hydroxydiphenyl ether), chlorhexidine (1,6-bis(4-chlorophenylbiguanidino)hexane) and TTC (3,4,4'-trichlorocarbanilide). Among the substances which reduce the growth of bacteria, mention may be made of transition-metal-chelating agents such as ethylenediaminetetraacetic acid (EDTA) or diethylenetriaminepentaacetic acid (DTPA);

ii) Substances which block the enzymatic reactions responsible for the formation of the odorous compounds. Mention may be made of arylsulfatase, 5-lipoxygenase, aminocylase and β-glucuronidase inhibitors;

iii) Unpleasant odour absorbers which "capture" or reduce the volatility of odorous compounds. Odour absorbers that may be mentioned include zeolites and cyclodextrins. It is also known that certain types of solid particles may be used as deodorants, such as the metal oxide silicates of patent application US 2005/063 928, the metal oxide particles modified with a transition metal in patent applications US 2005/084 464 and US 2005/084 474, aluminosilicates such as those described in patent application EP 1 658 863, and nanometric chitosan-based particles such as those described in patent U.S. Pat. No. 6,916,465; and iv) Antiperspirants, including aluminium and/or zirconium salts, which are the most commonly used as active agents. These aluminium salts also have intrinsic efficacy since they are antibacterial agents. They thus also play a direct role on the deodorant efficacy by reducing the number of bacteria responsible for the degradation of sweat.

Deodorant products are described in several books. An example that may be mentioned is Ullmann's Encyclopedia of Industrial Chemistry, "Skin Cosmetics", G. Schneider et al., http://onlinelibrary.wiley.com/doi/10.1002/14356007.a24_219/pdf, published online on 15 Jan. 2001, Wiley-VCH, DOI: 10.1002/14356007.a24_219, point 8 "Deodorants and Antiperspirants" (2012).

It is also known that certain types of solid particle may be used as deodorants, such as the metal oxide silicates of patent application US 2005/063 928; metal oxide particles modified with a transition metal in patents US 2005/084 464 and US 2005/084 474, aluminosilicates such as those described in patent application EP 1 658 863, and nanometric chitosan-based particles such as those described in patent U.S. Pat. No. 6,916,465.

It has already been proposed in patent application US 2004/0 001 897 to use in deodorant compositions fumed silica particles of colloidal structure modified with dimethylsilyl or trimethylsilyl groups, such as the product sold under the trade name Aerosil R972®.

It has also been proposed in patent application U.S. Pat. No. 4,605,554 to use in deodorant or antiperspirant compositions silicas hydrophobic-modified with organosilylamine groups such as $(CH_3O)_3Si(CH_2)_3$—$NH(CH_2)_2NH_2$ and $(CH_3O)_3(CH_3)SiCH_2CH(CH_3)_3$—$NHCH_2CH_2$—$NH_2$, organodisilazane groups such as $(CH_3)_3SiNHSi(CH_3)_3$ and $(C_4H_9)_3SiNHSi(C_4H_9)_3$, for instance the hydrophobic fumed silicas sold under the trade names Aerosil R972® and Tullanos 500®.

Particles of colloidal silica modified with a transition metal and an aminosilane are also known from patent U.S. Pat. No. 7,438,875, for instance 3-aminopropyltriethoxysilane (APTES), which have been used as deodorant active agent.

These prior art compositions based on hydrophobic-modified silica are not, however, entirely satisfactory in terms of deodorant efficacy.

There is thus still a real need to make novel cosmetic deodorant active agents in the form of siliceous material which have better efficacy than those mentioned previously.

The Applicant has discovered, surprisingly, that this objective can be achieved with a novel siliceous material that may be obtained by hydrolysis and condensation of at least one tetraalkoxysilane of formula (I) which will be defined in detail later and of at least one $C_7$-$C_{20}$-alkyltrialkoxysilane of formula (II) which will be defined in detail later.

This discovery forms the basis of the present invention.

The invention thus relates to the cosmetic use of a siliceous material that may be obtained by hydrolysis and condensation, in the presence of water, of at least one tetraalkoxysilane of formula (I) below:

$$Si(OR_2)_4 \quad (I)$$

and of an alkyltrialkoxysilane of formula (II) below:

$$R_1Si(OR_2)_3 \quad (II)$$

in which:

$R_1$ denotes a linear or branched $C_7$ to $C_{20}$ alkyl group, optionally interrupted in its chain with an O or S atom or with an NH group or a carbonyl group (CO), $R_2$ denotes a linear or branched $C_1$-$C_4$ alkyl group.

Preferentially, the siliceous material is present in a composition comprising a cosmetically acceptable medium.

The invention also relates to a cosmetic process for treating human body odour, in particular underarm odour and optionally human perspiration, which consists in applying to human keratin materials the said siliceous material or a composition containing the same in a cosmetically acceptable medium.

The invention also relates to a composition characterized in that it comprises, in a cosmetically acceptable medium, at least the said siliceous material and at least one deodorant agent other than the said siliceous material and/or at least one antiperspirant active agent.

For the purposes of the present invention, the term "physiologically acceptable medium" is intended to mean a medium that is suitable for the topical administration of a composition.

A physiologically acceptable medium is preferentially a cosmetically or dermatologically acceptable medium, that is to say a medium which is devoid of unpleasant odour or appearance and which is entirely compatible with the topical administration route.

In the present case, where the composition is intended for topical administration, that is to say for administration by application at the surface of the keratin material under consideration, such a medium is considered in particular to be physiologically acceptable when it does not cause stinging, tightness or redness unacceptable to the user.

The term "deodorant active agent" is intended to mean, in the context of the present invention, any active agent which, by itself alone, has the effect of masking, absorbing, improving and/or reducing the unpleasant odour resulting from the decomposition of human sweat.

The term "antiperspirant active agent" is intended to mean any substance which, by itself alone, has the effect of reducing the flow of sweat, of reducing the sensation on the skin of moisture associated with human sweat and of masking human sweat.

Siliceous Material

The siliceous material in accordance with the invention may be obtained by hydrolysis and condensation, in the presence of water, of at least one tetraalkoxysilane of formula (I) below:

$$Si(OR_2)_4 \quad (I)$$

and of an alkyltrialkoxysilane of formula (II) below:

$$R_1Si(OR_2)_3 \quad (II)$$

in which:

$R_1$ denotes a linear or branched $C_7$ to $C_{20}$ alkyl group, optionally interrupted in its chain with an O or S atom or with an NH group or a carbonyl group (CO), $R_2$ denotes a linear or branched $C_1$-$C_4$ alkyl group.

Preferably, $R_1$ represents a $C_8$ to $C_{18}$ alkyl group; $R_1$ may be an alkyl group chosen from n-octyl, n-decyl, n-dodecyl, n-tetradecyl, n-hexadecyl and n-octadecyl.

Preferably, $R_2$ represents a linear alkyl group comprising from 1 to 4 carbon atoms and more preferentially an ethyl group.

Compound (I) may be chosen from tetraethoxysilane (TEOS) and tetramethoxysilane (TMOS). Preferably, compound (I) is tetraethoxysilane (TEOS).

As compound (II), use may be made of n-octyltrimethoxysilane, n-dodecyltrimethoxysilane, n-octadecyltrimethoxysilane, n-octyltriethoxysilane, n-dodecyltriethoxysilane or n-octadecyltriethoxysilane, and mixtures thereof.

According to one embodiment, compound (II) is n-dodecyltriethoxysilane.

According to another embodiment of the invention, compound (II) is n-octadecyltriethoxysilane.

According to another embodiment of the invention, compound (II) is n-octyltriethoxysilane.

According to one embodiment of the invention, the siliceous material described previously may be obtained by hydrolysis and condensation of compounds (I) and (II) described previously and of at least one aminoalkyl trialkoxysilane of formula (III) below:

$$R_3Si(OR_4)_3$$

in which:

$R_3$ denotes a linear or branched, saturated or unsaturated $C_1$-$C_6$ hydrocarbon-based group or a cyclic $C_3$-$C_5$ hydrocarbon-based group, or denotes a $C_6$-$C_9$ aryl or $C_6$-$C_9$ aryloxy group, the said radicals being substituted with an amino group $NH_2$ or NHR with R denoting a $C_1$-$C_4$ alkyl group, $R_4$ denotes a linear or branched $C_1$-$C_4$ alkyl group.

Preferably, $R_3$ represents a $C_2$-$C_4$ hydrocarbon-based group substituted with an amino group $NH_2$ or NHR with R denoting a linear or branched $C_1$-$C_4$ alkyl group.

Preferably, $R_3$ represents a $C_2$-$C_4$ hydrocarbon-based group substituted with an amino group $NH_2$.

Preferably, $R_4$ represents a linear alkyl group comprising from 1 to 4 carbon atoms and more preferentially an ethyl group.

Preferably, the compound of formula (III) is chosen from 3-aminopropyltriethoxysilane (APTES), 3-aminoethyltriethoxysilane (AETES), N-(2-aminoethyl)-3-aminopropyltriethoxysilane, 3-(m-aminophenoxy)propyltrimethoxysilane, p-aminophenyltrimethoxysilane and N-(2-aminoethylaminomethyl)phenethyltrimethoxysilane.

Preferably, compound (III) is chosen from 3-aminopropyltriethoxysilane (APTES), 3-aminoethyltriethoxysilane (AETES) and N-(2-aminoethyl)-3-aminopropyltriethoxysilane.

Preferably, compound (III) is 3-aminopropyltriethoxysilane (APTES).

Advantageously, compounds (I) and (II) are used in a compound (I)/compound (II) weight ratio ranging from 0.9 to 100 and preferably ranging from 0.9 to 11.

Advantageously, compounds (I) and (III) are used in a compound (I)/compound (III) weight ratio ranging from 0.9 to 100 and preferably ranging from 0.9 to 21.

The siliceous material is obtained by hydrolysis and condensation of the silanes described previously. This reaction corresponds to a sol-gel polymerization.

The sol-gel polymerization is performed in the presence of water to bring about the hydrolysis of compounds (I) and (II) and optionally of compound (III), followed by their condensation.

The polymerization may be performed in the presence of an acidic catalyst, especially to accelerate the condensation reaction, for instance mineral acids such as hydrochloric acid or organic acids such as acetic acid.

The polymerization may be performed in the presence of a basic catalyst, for instance ammonia.

A list of catalysts used for catalysing the sol-gel reaction is described especially in the articles Catalysts and the structure of $SiO_2$ sol-gel films, Journal of Materials Science 35 (2000) 1835-184 and Sol-gel processing of silica: II. The role of the catalyst, Journal of Non-Crystalline Solids, Volume 87, Issues 1-2, 2 Oct. 1986, Pages 185-198.

The synthesis of this siliceous material is performed according to chemical reactions known to those skilled in the art, which are triggered when the reagents are placed in contact with water and optionally with a catalyst, which has the effect 1) of hydrolysing the alkoxy groups ($OR_2$) of the silanes (I) and (II) to hydroxyl groups, and then 2) of condensing the hydrolysed products to lead 3) to the polymerization of the system.

When the sol-gel polymerization reaction is complete, the siliceous material obtained is advantageously recovered according to the known techniques by filtration or centrifugation, and may be washed especially with water and/or ethanol, and then optionally dried. A siliceous material in powder form is thus obtained.

In the compositions of the invention, the concentration of the siliceous material in accordance with the invention preferably ranges from 0.1% to 100%, more preferentially from 1% to 70% and even more preferentially from 1% to 50% by weight relative to the total weight of the composition.

Cosmetic Composition

Additional Deodorant Active Agents

The composition according to the invention may contain one or more additional deodorant active agents other than the siliceous materials of the invention, for instance:
- bacteriostatic agents or other bactericidal agents such as 2,4,4'-trichloro-2'-hydroxydiphenyl ether (triclosan), 2,4-dichloro-2'-hydroxydiphenyl ether, 3',4',5'-trichlorosalicylanilide, 1-(-3',4'-dichlorophenyl)-3-(4'-chlorophenyl)urea (triclocarban) or 3,7,11-trimethyldodeca-2,5,10-trienol (Farnesol); quaternary ammonium salts, for instance cetyltrimethylammonium salts, cetylpyridinium salts; chlorhexidine and salts; diglyceryl monocaprate, diglyceryl monolaurate or glyceryl monolaurate; polyhexamethylene biguanide salts;
- zinc salts, such as zinc salicylate, zinc phenolsulfonate, zinc pyrrolidonecarboxylate (more commonly known as zinc pidolate), zinc sulfate, zinc chloride, zinc lactate, zinc gluconate, zinc ricinoleate, zinc glycinate, zinc carbonate, zinc citrate, zinc chloride, zinc laurate, zinc oleate, zinc orthophosphate, zinc stearate, zinc tartrate, zinc lactate, zinc acetate or mixtures thereof;
- odour absorbers, such as zeolites, cyclodextrins, metal oxide silicates, such as those described in Application US 2005/063928, metal oxide particles modified by a transition metal, such as described in applications US 2005/084464 and US 2005/084474, aluminosilicates, such as those described in Application EP 1 658 863, or particles of chitosan derivatives, such as those described in patent U.S. Pat. No. 6,916,465;
- substances which block the enzymatic reactions responsible for the formation of odorous compounds, such as arylsulfatase, 5-lipoxygenase, aminocylase or β-glucuronidase inhibitors;

and mixtures thereof.

The additional deodorant active agents may be present in the composition according to the invention in a proportion of from 0.01% to 10% by weight and preferably in a proportion of from 0.1% to 5% by weight relative to the total weight of the composition.

Antiperspirant Active Agents

The composition according to the invention may contain one or more antiperspirant active agents.

The term "antiperspirant active agent" is intended to mean any substance which, by itself alone, has the effect of reducing the flow of sweat, of reducing the sensation on the skin of moisture associated with human sweat and of masking human sweat.

The antiperspirant active agents are preferably chosen from aluminium and/or zirconium salts; complexes of zirconium hydroxychloride and of aluminium hydroxychloride with an amino acid, such as those described in U.S. Pat. No. 3,792,068, commonly known as "ZAG" complexes. Such complexes are generally known under the name ZAG (when the amino acid is glycine). The ZAG complexes ordinarily exhibit an Al/Zr quotient ranging from approximately 1.67 to 12.5 and a metal/Cl quotient ranging from approximately 0.73 to 1.93. Mention may be made, among these products, of aluminium zirconium octachlorohydrex GLY, aluminium zirconium pentachlorohydrex GLY, aluminium zirconium tetrachlorohydrate GLY and aluminium zirconium trichlorohydrate GLY.

Among the aluminium salts that may be mentioned are aluminium chlorohydrate, aluminium chlorohydrex, aluminium chlorohydrex PEG, aluminium chlorohydrex PG, aluminium dichlorohydrate, aluminium dichlorohydrex PEG, aluminium dichlorohydrex PG, aluminium sesquichlorohydrate, aluminium sesquichlorohydrex PEG, aluminium sesquichlorohydrex PG, alum salts, aluminium sulfate, aluminium zirconium octachlorohydrate, aluminium zirconium pentachlorohydrate, aluminium zirconium tetrachlorohydrate, aluminium zirconium trichlorohydrate and more particularly the aluminium hydroxychloride sold by the company Reheis under the name Reach 301® or by the company Guilini Chemie under the name Aloxicoll PF 40®. Aluminium zirconium salts are, for example, the salt sold by the company Reheis under the name Reach AZP-908-SUF®.

Use will more particularly be made of aluminium chlorohydrate in the activated or non-activated form.

The antiperspirant active agents can be present in the composition according to the invention in a proportion of from 0.001% to 30% by weight and preferably in a proportion of from 0.5% to 25% by weight, relative to the total weight of the composition.

Galenical Forms

The composition according to the invention may be in any galenical form conventionally used for topical application and especially in the form of aqueous gels, or aqueous or aqueous-alcoholic solutions. By adding a fatty or oily phase, it may also be in the form of dispersions of lotion type, emulsions of liquid or semi-liquid consistency of milk type, obtained by dispersing a fatty phase in an aqueous phase (O/W) or conversely (W/O), or suspensions or emulsions of soft, semi-solid or solid consistency of the cream or gel type, or alternatively multiple emulsions (W/O/W or O/W/O), microemulsions, vesicular dispersions of ionic and/or nonionic type, or wax/aqueous phase dispersions. These compositions are prepared according to the usual methods.

The compositions may especially be packaged in pressurized form in an aerosol device or in a pump-action bottle; packaged in a device equipped with a perforated wall, in particular a grate; packaged in a device equipped with a ball applicator ("roll-on"); packaged in the form of wands (sticks) or in the form of loose or compacted powder. In this regard, they contain the ingredients generally used in products of this type, which are well known to those skilled in the art.

According to another specific form of the invention, the compositions according to the invention can be anhydrous.

The term "anhydrous composition" is intended to mean a composition containing less than 2% by weight of water, indeed less than 0.5% of water, and in particular devoid of water, the water not being added during the preparation of the composition but corresponding to the residual water contributed by the mixed ingredients.

According to another particular form of the invention, the compositions according to the invention may be solid, in particular in wand or stick form.

The term "solid composition" is intended to mean that the measurement of the maximum force measured by texturometry during the penetration of a probe into the sample of formula must be at least equal to 0.25 newtons, in particular at least equal to 0.30 newtons and in particular at least equal to 0.35 newtons, assessed under precise measurement conditions as follows.

The formulae are poured hot into jars with a diameter of 4 cm and a depth of 3 cm. Cooling is carried out at room temperature. The hardness of the formulae produced is measured after an interval of 24 hours. The jars containing the samples are characterized in texturometry using a texture analyzer such as the machine sold by the company Rheo TA-XT2, according to the following protocol: a stainless-steel ball probe 5 mm in diameter is brought into contact with the sample at a speed of 1 mm/s. The measurement system detects the interface with the sample, with a detection threshold equal to 0.005 newtons. The probe penetrates 0.3 mm into the sample, at a speed of 0.1 mm/s. The measuring machine records the change in force measured in compression over time, during the penetration phase. The hardness of the sample corresponds to the average of the maximum force values detected during penetration, over at least three measurements.

Aqueous Phase

The compositions according to the invention intended for cosmetic use may comprise at least one aqueous phase. They are in particular formulated as aqueous lotions or as water-in-oil or oil-in-water emulsions or as multiple emulsions (oil-in-water-in-oil or water-in-oil-in-water triple emulsions (such emulsions are known and described, for example, by C. Fox in "Cosmetics and Toiletries"—November 1986—Vol. 101—pages 101-112)).

The aqueous phase of said compositions contains water and generally other water-soluble or water-miscible solvents. The water-soluble or water-miscible solvents comprise short-chain, for example $C_1$-$C_4$, monoalcohols, such as ethanol or isopropanol; diols or polyols, such as ethylene glycol, 1,2-propylene glycol, 1,3-butylene glycol, hexylene glycol, diethylene glycol, dipropylene glycol, 2-ethoxyethanol, diethylene glycol monomethyl ether, triethylene glycol monomethyl ether and sorbitol. Use will more particularly be made of propylene glycol and glycerol, and propane-1, 3-diol.

The composition according to the invention preferably has a pH ranging from 3 to 9, according to the support chosen.

Emulsifiers
Oil-in-water Emulsifiers

As emulsifiers that may be used in the oil-in-water emulsions or oil-in-water-in-oil triple emulsions, examples that may be mentioned include nonionic emulsifiers such as oxyalkylenated (more particularly polyoxyethylenated) fatty acid esters of glycerol; oxyalkylenated fatty acid esters of sorbitan; oxyalkylenated (oxyethylenated and/or oxypropylenated) fatty acid esters; oxyalkylenated (oxyethylenated and/or oxypropylenated) fatty alcohol ethers; sugar esters such as sucrose stearate; and mixtures thereof, such as the mixture of glyceryl stearate and PEG-40 stearate.

Mention may also be made of fatty alcohol/alkylpolyglycoside emulsifying mixtures as described in patent applications WO 92/06778, WO 95/13863 and WO 98/47610, for instance the commercial products sold by the company SEPPIC under the name Montanov®.

Water-in-oil Emulsifiers

Among the emulsifiers that may be used in the water-in-oil emulsions or water-in-oil-in-water-in-oil triple emulsions, examples that may be mentioned include alkyl dimethicone copolyols, for instance Cetyl PEG/PPG-10/1 Dimethicone and more particularly the mixture Cetyl PEG/PPG-10/1 Dimethicone and Dimethicone (INCI name), for instance the product sold under the trade name Abil EM90® by the company Goldschmidt, or alternatively the mixture (Polyglyceryl-4 Stearate and Cetyl PEG/PPG-10 (and) Dimethicone (and) Hexyl Laurate), for instance the product sold under the trade name Abil WE09® by the same company.

Among the water-in-oil emulsifiers, mention may also be made of dimethicone copolyols, for instance PEG-18/PPG-18 Dimethicone and more particularly the mixture Cyclopentasiloxane (and) PEG-18/PPG-18 Dimethicone (INCI name), such as the product sold by the company Dow Corning under the trade name Silicone DC5225 C® or KF-6040® from the company Shin-Etsu.

Among the water-in-oil emulsifiers, mention may also be made of nonionic emulsifiers derived from fatty acids and polyol, alkylpolyglycosides (APG) and sugar esters, and mixtures thereof.

As nonionic emulsifiers derived from fatty acids and polyols, use may be made especially of fatty acid esters of polyols, the fatty acid especially containing a $C_8$-$C_{24}$ alkyl chain, and the polyols being, for example, glycerol and sorbitan.

Mention may in particular be made, as fatty acid esters of polyols, of isostearic acid esters of polyols, stearic acid esters of polyols, and mixtures thereof, in particular isostearic acid esters of glycerol and/or sorbitan.

Stearic acid esters of polyols that may especially be mentioned include the polyethylene glycol esters, for instance PEG-30 Dipolyhydroxystearate, such as the product sold under the name Arlacel P135® by the company ICI.

Glycerol and/or sorbitan esters that may be mentioned, for example, include polyglyceryl isostearate, such as the product sold under the name Isolan GI 34® by the company Goldschmidt; sorbitan isostearate, such as the product sold under the name Arlacel 987 by the company ICI; sorbitan glyceryl isostearate, such as the product sold under the name Arlacel 986® by the company ICI, the mixture of sorbitan isostearate and polyglyceryl isostearate (3 mol) sold under the name Arlacel 169® by the company Uniqema, and mixtures thereof.

The emulsifier may also be chosen from alkylpolyglycosides with an HLB of less than 7, for example those represented by the general formula (1) below:

$$R'—O—(G)x \tag{1}$$

in which R' represents a branched and/or unsaturated alkyl radical comprising from 14 to 24 carbon atoms, G represents a reduced sugar comprising 5 or 6 carbon atoms, and x is a value ranging from 1 to 10 and preferably from 1 to 4, and G especially denotes glucose, fructose or galactose.

The unsaturated alkyl radical may comprise one or more ethylenic unsaturations, and in particular one or two ethylenic unsaturations.

As alkylpolyglycosides of this type, mention may be made of alkylpolyglucosides (G=glucose in formula (I)), and especially the compounds of formula (I) in which R more particularly represents an oleyl radical (unsaturated $C_{18}$ radical) or isostearyl (saturated $C_{18}$ radical), G denotes glucose, and x is a value ranging from 1 to 2, especially isostearyl glucoside or oleyl glucoside, and mixtures thereof. This alkylpolyglucoside may be used as a mixture with a coemulsifier, more especially with a fatty alcohol and especially a fatty alcohol containing the same fatty chain as that of the alkylpolyglucoside, i.e. comprising from 14 to 24 carbon atoms and containing a branched and/or unsaturated chain, and for example isostearyl alcohol when the alkylpolyglucoside is isostearyl glucoside, and oleyl alcohol when the alkylpolyglucoside is oleyl glucoside, optionally in the form of a self-emulsifying composition, as described, for example, in the document WO-A-92/06778.

Mention may also be made of succinic-terminated polyolefins, for instance esterified succinic-terminated polyisobutylenes and salts thereof, especially the diethanolamine salts, such as the products sold under the names Lubrizol 2724®, Lubrizol 2722® and Lubrizol 5603 by the company Lubrizol® or the commercial product Chemcinnate 2000®.

The total amount of emulsifiers in the composition will preferably be, in the composition according to the invention, at active material contents ranging from 1% to 8% by weight and more particularly from 2% to 6% by weight, relative to the total weight of the composition.

Fatty Phase

The compositions according to the invention may contain at least one water-immiscible organic liquid phase, known as a fatty phase. This phase generally comprises one or more hydrophobic compounds which render said phase water-immiscible. The said phase is liquid (in the absence of structuring agent) at room temperature (20-25° C.). Preferentially, the water-immiscible organic liquid phase in accordance with the invention generally comprises at least one volatile oil and/or one non-volatile oil and optionally at least one structuring agent.

The term "oil" means a fatty substance that is liquid at room temperature (25° C.) and atmospheric pressure (760 mmHg, i.e. $10^5$ Pa). The oil may be volatile or non-volatile.

For the purposes of the invention, the term "volatile oil" means an oil that is capable of evaporating on contact with the skin or the keratin fibre in less than one hour, at room temperature and atmospheric pressure. The volatile oils of the invention are volatile cosmetic oils which are liquid at room temperature and which have a non-zero vapour pressure, at room temperature and atmospheric pressure, ranging in particular from 0.13 Pa to 40 000 Pa ($10^{-3}$ to 300 mmHg), in particular ranging from 1.3 Pa to 13 000 Pa (0.01 to 100 mmHg) and more particularly ranging from 1.3 Pa to 1300 Pa (0.01 to 10 mmHg).

The term "non-volatile oil" means an oil that remains on the skin or the keratin fibre at room temperature and atmospheric pressure for at least several hours, and that especially has a vapour pressure of less than $10^{-3}$ mmHg (0.13 Pa).

The oil can be chosen from any physiologically acceptable oils and in particular cosmetically acceptable oils; in particular mineral, animal, vegetable or synthetic oils; in particular volatile or non-volatile hydrocarbon-based oils and/or silicone oils and/or fluoro oils, and mixtures thereof.

More specifically, the term "hydrocarbon-based oil" is intended to mean an oil mainly comprising carbon and hydrogen atoms and optionally one or more functions chosen from hydroxyl, ester, ether and carboxylic functions. Generally, the oil has a viscosity of from 0.5 to 100 000 mPa·s, preferably from 50 to 50 000 mPa·s and more preferably from 100 to 300 000 mPa·s.

As examples of volatile oils that may be used in the invention, mention may be made of:
volatile hydrocarbon-based oils chosen from hydrocarbon-based oils containing from 8 to 16 carbon atoms, and in particular $C_8$-$C_{16}$ isoalkanes of petroleum origin (also known as isoparaffins), for instance isododecane (also known as 2,2,4,4,6-pentamethylheptane), isodecane and isohexadecane, and for example the oils sold under the trade names Isopar or Permethyl, branched $C_8$-$C_{16}$ esters and isohexyl neopentanoate, and mixtures thereof. Use may also be made of other volatile hydrocarbon-based oils, such as petroleum distillates, in particular those sold under the name Shell Solt by the company Shell; and volatile linear alkanes, such as those described in Patent Application DE10 2008 012 457 from the company Cognis;
volatile silicones, for instance linear or cyclic volatile silicone oils, in particular those with a viscosity of ≤8 centistokes ($8\times10^{-6}$ m²/s) and especially containing from 2 to 7 silicon atoms, these silicones optionally comprising alkyl or alkoxy groups containing from 1 to 10 carbon atoms. As volatile silicone oils that may be used in the invention, mention may be made especially of octamethylcyclotetrasiloxane, decamethylcyclopentasiloxane, dodecamethylcyclohexasiloxane, heptamethylhexyltrisiloxane, heptamethyloctyltrisiloxane, hexamethyldisiloxane, octamethyltrisiloxane, decamethyltetrasiloxane and dodecamethylpentasiloxane;
and mixtures thereof.

Mention may also be made of linear volatile alkyltrisiloxane oils of general formula (I):

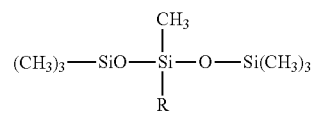

where R represents an alkyl group comprising from 2 to 4 carbon atoms, one or more hydrogen atoms of which can be replaced by a fluorine or chlorine atom.

Mention may be made, among the oils of general formula (I), of:
3-butyl-1,1,1,3,5,5,5-heptamethyltrisiloxane,
3-propyl-1,1,1,3,5,5,5-heptamethyltrisiloxane, and
3-ethyl-1,1,1,3,5,5,5-heptamethyltrisiloxane,
corresponding to the oils of formula (I) for which R is, respectively, a butyl group, a propyl group or an ethyl group.

As examples of nonvolatile oils that may be used in the invention, mention may be made of:
hydrocarbon-based oils of animal origin, such as perhydrosqualene;
vegetable hydrocarbon-based oils, such as liquid triglycerides of fatty acids containing 4 to 24 carbon atoms, such as heptanoic or octanoic acid triglycerides, or else wheat germ oil, olive oil, sweet almond oil, palm oil, rapeseed oil, cottonseed oil, alfalfa oil, poppy seed oil, pumpkin seed oil, blackcurrant oil, evening primrose oil, millet oil, barley oil, quinoa oil, rye oil, safflower oil, candlenut oil, passionflower oil, musk rose oil, sunflower oil, maize oil, soybean oil, marrow oil, grape seed oil, sesame oil, hazelnut oil, apricot oil, macadamia oil, castor oil, avocado oil, caprylic/capric acid triglycerides, such as those sold by the company Stearineries Dubois or those sold under the names Miglyol 810, 812 and 818 by the company Dynamit Nobel, jojoba oil or shea butter oil;

linear or branched hydrocarbons of mineral or synthetic origin, such as liquid paraffins and derivatives thereof, petroleum jelly, polydecenes, polybutenes, hydrogenated polyisobutene, such as Parleam, or squalane;

synthetic ethers containing from 10 to 40 carbon atoms;

synthetic esters, especially of fatty acids, for instance the oils of formula $R_1COOR_2$ in which $R_1$ represents a linear or branched higher fatty acid residue containing from 1 to 40 carbon atoms and $R_2$ represents a hydrocarbon-based chain, which is especially branched, containing from 1 to 40 carbon atoms, with $R_1 + R_2 \geq 10$, for instance purcellin oil (cetostearyl octanoate), isononyl isononanoate, isopropyl myristate, isopropyl palmitate, $C_{12}$-$C_{15}$ alkyl benzoates, hexyl laurate, diisopropyl adipate, isononyl isononanoate, 2-ethylhexyl palmitate, 2-octyldodecyl stearate, 2-octyldodecyl erucate, isostearyl isostearate or tridecyl trimellitate; alcohol or polyalcohol octanoates, decanoates or ricinoleates, for instance propylene glycol dioctanoate; hydroxylated esters, for instance isostearyl lactate, octyl hydroxystearate, octyldodecyl hydroxystearate, diisostearyl malate, triisocetyl citrate, and fatty alcohol heptanoates, octanoates or decanoates; polyol esters, for instance propylene glycol dioctanoate, neopentyl glycol diheptanoate or diethylene glycol diisononanoate; and pentaerythritol esters, for instance pentaerythrityl tetra isostearate;

fatty alcohols that are liquid at room temperature, containing a branched and/or unsaturated carbon-based chain containing from 12 to 26 carbon atoms, for instance octyldodecanol, isostearyl alcohol, 2-butyloctanol, 2-hexyldecanol, 2-undecylpentadecanol or oleyl alcohol;

higher fatty acids such as oleic acid, linoleic acid or linolenic acid;

carbonates;

acetates;

citrates;

fluoro oils that are optionally partially hydrocarbon-based and/or silicone-based, for instance fluorosilicone oils, fluoro polyethers and fluorosilicones as described in document EP-A-847 752;

silicone oils, for instance linear or cyclic non-volatile polydimethylsiloxanes (PDMS); polydimethylsiloxanes comprising alkyl, alkoxy or phenyl groups, which are pendant or at the end of a silicone chain, these groups containing from 2 to 24 carbon atoms; phenyl silicones, for instance phenyl trimethicones, phenyl dimethicones, phenyl trimethylsiloxy diphenyl siloxanes, diphenyl dimethicones, diphenyl methyldiphenyl trisiloxanes and 2-phenylethyl trimethylsiloxy silicates, and mixtures thereof.

Additives

The cosmetic compositions according to the invention may also comprise cosmetic adjuvants chosen from softeners, antioxidants, opacifiers, stabilizers, moisturizers, vitamins, bactericides, preserving agents, polymers, fragrances, a structuring agent for a fatty phase, in particular chosen from waxes, pasty compounds, and mineral or organic lipophilic gelling agents; organic or mineral fillers; thickeners or suspending agents, propellants or any other ingredient usually used in cosmetics for this type of application.

Needless to say, a person skilled in the art will take care to select this or these optional additional compounds such that the advantageous properties intrinsically associated with the cosmetic composition in accordance with the invention are not, or are not substantially, adversely affected by the envisaged addition(s).

Wax(es)

The wax is in general a lipophilic compound that is solid at room temperature (25° C.), with a reversible solid/liquid change in state, having a melting point of greater than or equal to 30° C., which may be up to 200° C. and in particular up to 120° C.

In particular, the waxes that are suitable for use in the invention may have a melting point of greater than or equal to 45° C. and in particular of greater than or equal to 55° C.

For the purposes of the invention, the melting point corresponds to the temperature of the most endothermic peak observed in thermal analysis (DSC) as described in the standard ISO 11357-3; 1999. The melting point of the wax may be measured using a differential scanning calorimeter (DSC), for example the calorimeter sold under the name MDSC 2920® by the company TA Instruments.

The measuring protocol is as follows:

A sample of 5 mg of wax placed in a crucible is subjected to a first temperature rise ranging from −20° C. to 100° C., at a heating rate of 10° C./minute, it is then cooled from 100° C. to −20° C. at a cooling rate of 10° C./minute and it is finally subjected to a second temperature rise ranging from −20° C. to 100° C. at a heating rate of 5° C./minute. During the second temperature rise, the variation in the difference in power absorbed by the empty crucible and by the crucible containing the sample of wax is measured as a function of the temperature. The melting point of the compound is the temperature value corresponding to the top of the peak of the curve representing the variation in the difference in power absorbed as a function of the temperature.

The waxes that may be used in the compositions according to the invention are chosen from waxes that are solid at room temperature of animal, vegetable, mineral or synthetic origin, and mixtures thereof.

As illustrations of waxes that are suitable for the invention, mention may be made especially of hydrocarbon-based waxes, for instance beeswax, lanolin wax, Chinese insect waxes, rice bran wax, carnauba wax, candelilla wax, ouricury wax, esparto grass wax, berry wax, shellac wax, Japan wax and sumach wax; montan wax, orange wax and lemon wax, refined sunflower wax sold under the name Sunflower Wax® by Koster Keunen, microcrystalline waxes, paraffins and ozokerite; polyethylene waxes, the waxes obtained by Fischer-Tropsch synthesis and waxy copolymers, and also esters thereof.

Mention may also be made of waxes obtained by catalytic hydrogenation of animal or plant oils containing linear or branched $C_8$-$C_{32}$ fatty chains. Mention may especially be made, among these waxes, of isomerized jojoba oil such as the trans-isomerized partially hydrogenated jojoba oil manufactured or sold by the company Desert Whale under the commercial reference Iso-Jojoba-50®, hydrogenated sunflower oil, hydrogenated castor oil, hydrogenated coconut oil, hydrogenated lanolin oil and bis(1,1,1-trimethylolpropane) tetrastearate sold under the name Hest 2T-4S® by the company Heterene.

Mention may also be made of silicone waxes ($C_{30-45}$ alkyl dimethicone) and fluoro waxes.

The waxes obtained by hydrogenation of castor oil esterified with cetyl alcohol, sold under the names Phytowax ricin 16L64® and 22L73® by the company Sophim, may also be used. Such waxes are described in patent application FR-A-2 792 190.

As wax, use may be made of a $C_{20}$-$C_{40}$ alkyl (hydroxystearyloxy)stearate (the alkyl group comprising from 20 to 40 carbon atoms), alone or as a mixture.

Such a wax is especially sold under the names Kester Wax K 82 P®, Hydroxypolyester K 82 P® and Kester Wax K 80 P® by the company Koster Keunen.

As microwaxes that may be used in the compositions according to the invention, mention may be made especially of carnauba microwaxes, such as the product sold under the name MicroCare 350® by the company Micro Powders, synthetic microwaxes, such as the product sold under the name MicroEase 114S® by the company Micro Powders, microwaxes consisting of a mixture of carnauba wax and polyethylene wax, such as the products sold under the names Micro Care 300® and 310® by the company Micro Powders, microwaxes consisting of a mixture of carnauba wax and of synthetic wax, such as the product sold under the name Micro Care 325® by the company Micro Powders, polyethylene microwaxes, such as the products sold under the names Micropoly 200®, 220®, 220L® and 250S® by the company Micro Powders, the commercial products Performalene 400 Polyethylene® and Performalene 500-L Polyethylene® from New Phase Technologies, Performalene 655, Polyethylene® or paraffin waxes, for instance the wax having the INCI name Microcrystalline Wax and Synthetic Wax and sold under the trade name Microlease by the company Sochibo; polytetrafluoroethylene microwaxes such as those sold under the names Microslip 519® and 519 L® by the company Micro Powders.

Pasty Compounds

For the purposes of the present invention, the term "pasty compound" means a lipophilic fatty compound that undergoes a reversible solid/liquid change of state, having in the solid state an anisotropic crystal organization, and comprising, at a temperature of 23° C., a liquid fraction and a solid fraction.

The pasty compound is preferably chosen from synthetic compounds and compounds of plant origin. A pasty compound may be obtained by synthesis from starting materials of plant origin.

The pasty compound may be advantageously chosen from:
  lanolin and derivatives thereof,
  polymeric or non-polymeric silicone compounds,
  polymeric or non-polymeric fluoro compounds,
  vinyl polymers, especially:
  olefin homopolymers,
  olefin copolymers,
  hydrogenated diene homopolymers and copolymers,
  linear or branched oligomers, homopolymers or copolymers of alkyl (meth)acrylates preferably containing a $C_8$-$C_{30}$ alkyl group,
  homo- and copolymeric oligomers of vinyl esters containing $C_8$-$C_{30}$ alkyl groups,
  homo- and copolymeric oligomers of vinyl ethers having $C_8$-$C_{30}$ alkyl groups,
  liposoluble polyethers resulting from polyetherification between one or more $C_2$-$C_{100}$, preferably $C_2$-$C_{50}$, diols, esters,
  mixtures thereof.

Lipophilic Gelling Agents

Lipophilic gelling agents that may be mentioned include optionally modified clays, for instance hectorites modified with a $C_{10}$ to $C_{22}$ ammonium chloride, for instance hectorite modified with distearyldimethylammonium chloride, for instance the product sold under the name Bentone 38V® by the company Elementis.

Thickeners

The thickeners may be chosen from carboxyvinyl polymers, such as Carbopols (Carbomers) and the Pemulens (acrylate/C10-C30 alkyl acrylate copolymer); polyacrylamides, for instance the crosslinked copolymers sold under the names Sepigel 305® (CTFA name: polyacrylamide/C13-14 isoparaffin/Laureth 7) or Simulgel 600® (CTFA name: acrylamide/sodium acryloyldimethyltaurate copolymer/isohexadecane/polysorbate 80) by the company SEPPIC; 2-acrylamido-2-methylpropanesulfonic acid polymers and copolymers, optionally crosslinked and/or neutralized, for instance poly(2-acrylamido-2-methylpropanesulfonic acid) sold by the company Hoechst under the trade name Hostacerin AMPS® (CTFA name: ammonium polyacryloyldimethyltaurate or Simulgel 800® sold by the company SEPPIC (CTFA name: sodium polyacryloyldimethyltaurate/polysorbate 80/sorbitan oleate); copolymers of 2-acrylamido-2-methylpropanesulfonic acid and of hydroxyethyl acrylate, for instance Simulgel NS and Sepinov EMT 10® sold by the company SEPPIC; cellulose derivatives such as hydroxyethyl cellulose or cetyl hydroxyethyl cellulose; polysaccharides and especially gums such as xanthan gum and hydroxypropyl guar gums; silicas, for instance Bentone Gel MIO® sold by the company NL Industries or Veegum Ultra® sold by the company Polyplastic.

Suspending Agents

In order to improve the homogeneity of the product, use may additionally be made of one or more suspending agents which are preferably chosen from hydrophobic modified montmorillonite clays, such as hydrophobic modified bentonites or hectorites. Examples that may be mentioned include the product Stearalkonium Bentonite (CTFA name) (product of reaction of bentonite and the quaternary ammonium stearalkonium chloride) such as the commercial product sold under the name Tixogel MP 250® by the company Sud Chemie Rheologicals, United Catalysts Inc. or the product Disteardimonium Hectorite (CTFA name) (product of reaction of hectorite and distearyldimonium chloride) sold under the name Bentone 38 or Bentone Gel by the company Elementis Specialities.

Other suspension agents may be used, in the present case in hydrophilic media (aqueous and/or ethanolic). They can be derivatives of cellulose, xanthan, guar, starch, locust bean or agar agar.

The suspending agents are preferably present in amounts ranging from 0.1% to 5% by weight and more preferentially from 0.2% to 2% by weight relative to the total weight of the composition.

The amounts of these various constituents that may be present in the cosmetic composition according to the invention are those conventionally used in compositions for treating perspiration.

Aerosols

The compositions according to the invention may also be pressurized and may be packaged in an aerosol device formed by:

(A) a container comprising an antiperspirant composition as defined previously, (B) at least one propellant and a means for dispensing said aerosol composition.

The propellants generally used in products of this type and that are well known to those skilled in the art are, for instance, dimethyl ether (DME); volatile hydrocarbons such as n-butane, propane, isobutane and mixtures thereof, optionally with at least one chlorohydrocarbon and/or fluorohydrocarbon; among these derivatives, mention may be made of the compounds sold by the company DuPont de Nemours under the names Freon® and Dymel®, and in particular monofluorotrichloromethane, difluorodichloromethane, tetrafluorodichloroethane and 1,1-difluoroethane sold especially under the trade name Dymel 152 A® by the company DuPont. Carbon dioxide, nitrous oxide, nitrogen or compressed air may also be used as propellant.

The compositions comprising perlite particles as defined above and the propellant(s) can be in the same compartment or in different compartments in the aerosol container. According to the invention, the concentration of propellant generally varies from 5% to 95% by weight pressurized and more preferentially from 50% to 85% by weight, relative to the total weight of the pressurized composition.

The dispensing means, which forms a part of the aerosol device, is generally formed by a dispensing valve controlled by a dispensing head, which itself comprises a nozzle via which the aerosol composition is vaporized. The container containing the pressurized composition may be opaque or transparent. It can be made of glass, of polymer or of metal, optionally covered with a protective lacquer layer.

The terms "between . . . and . . . " and "ranging from . . . to . . . " should be understood as being limits inclusive, unless otherwise specified.

The examples which follow illustrate the present invention without limiting the scope thereof.

PREPARATION EXAMPLES

Example 1

20 g of tetraethoxysilane and 20 g of n-octyltriethoxysilane were added to 200 ml of ethanol. The mixture was stirred for 2 minutes. A mixture of 95 ml of water and 15 ml of 35% hydrochloric acid in water was added dropwise and the reaction mixture was stirred vigorously for 10 minutes. Next, 28% aqueous ammonia solution was added dropwise to bring the pH to 9. The reaction mixture was stirred vigorously for 24 hours and then poured into 2 litres of water, filtered and then washed three times with 500 ml of ethanol, and finally dried under vacuum at 70° C. for 1 hour. 10.1 g of a white powder were obtained.

Example 2

20.8 g of tetraethoxysilane and 2.08 g of n-octyltriethoxysilane were added to 350 ml of ethanol. The mixture was stirred for 2 minutes. A mixture of 50 ml of water and 10 ml of 35% hydrochloric acid in water was added dropwise and the reaction mixture was stirred vigorously for 10 minutes. Next, 28% aqueous ammonia solution was added dropwise to bring the pH to 9. The reaction mixture was stirred vigorously for 22 hours and then centrifuged at 4000 rpm for 4 minutes. The precipitate was triturated with 1 litre of ethanol and then centrifuged at 4000 rpm for 4 minutes. The precipitate was triturated and then centrifuged at 4000 rpm for 4 minutes with 200 ml of ethanol. The trituration and centrifugation cycle was repeated. The powder obtained was dried under vacuum and then poured into 500 ml of water. 10 ml of acetone were added. The mixture was stirred for 30 minutes and then filtered and the precipitate was washed with water (3 times 300 ml). The white powder was dried under vacuum at 80° C. for 24 hours. 4.1 g of a white powder were obtained.

Example 3

The powder was prepared according to the procedure of Example 2, using 20 g of tetraethoxysilane, 2 g of n-octadecyltriethoxysilane and 350 ml of ethanol. 6 g of a white powder were obtained.

Example 4

The powder was prepared according to the procedure of Example 2, using 18.2 g of tetraethoxysilane, 1.82 g of n-dodecyltriethoxysilane and 350 ml of ethanol. 6 g of a white powder were obtained.

Example 5

20 g of tetraethoxysilane, 20 g of 3-aminopropyltriethoxysilane and 20 g of n-octyltriethoxysilane were added to 300 ml of ethanol. The mixture was stirred for 2 minutes. A mixture of 120 ml of water and 15 ml of 35% hydrochloric acid was added dropwise and the reaction mixture was stirred vigorously for 30 minutes. Next, 28% aqueous ammonia solution was added dropwise to bring the pH to 9. The reaction mixture was stirred vigorously for 24 hours and then poured into 2 litres of water and centrifuged at 4000 rpm for 4 minutes. The precipitate was washed and then centrifuged three times with ethanol (500 ml) and then three times with water (500 ml). The powder obtained was dried under vacuum at 80° C. for 24 hours. 7 g of a white powder were obtained.

The morphology of the particles of the powder obtained was characterized using an optical microscopy machine (Morphologi G3® from the company Malvern Instruments). 2 mg of the powder were sonicated in 1 ml of water for 5 minutes and then analysed. The particles have a mean diameter of 1.3 microns and a mean circularity of 0.76.

Example 6

The powder was prepared according to the procedure of Example 5, using 20 g of tetraethoxysilane, 1 g of n-octyltriethoxysilane and 350 ml of ethanol. 7.4 g of a white powder were obtained.

Comparative Tests of Deodorant Efficacy

Two deodorant pastes according to the invention containing the siliceous material of Example 1 (formula C) and of Example 5 (formula D) and two deodorant pastes similar to paste C and to paste D, in which the siliceous material was replaced, respectively, with untreated silica (Sunsphere H51 (formula A) and with hydrophobic fumed silica Aerosil R972 (formula B), were prepared.

The formulae are as follows (contents expressed as weight percentages):

|  | Formula | | | |
|---|---|---|---|---|
| Ingredients (INCI name) | A | B | C | D |
| Polydimethylsiloxane (10 cSt) (Xiameter PMX-200 ®) | 37 | 37 | 37 | 37 |
| Isopropyl palmitate | 25 | 25 | 25 | 25 |
| Isopropyl myristate | 23 | 23 | 23 | 23 |

-continued

| Ingredients (INCI name) | Formula | | | |
|---|---|---|---|---|
| | A | B | C | D |
| Dimethiconol (Xiameter PMX1502 ®) | 6 | 6 | 6 | 6 |
| Polydimethylsiloxane (1000 cSt) (Dow Corning silicone fluid SH 200 ®) | 3 | 3 | 3 | 3 |
| Unmodified silica (Sunsphere H 51) | 6 | — | — | — |
| Hydrophilic fumed silica (Aerosil R 972 ®) | — | 6 | — | — |
| Siliceous material of Example 1 | — | — | 6 | — |
| Siliceous material of Example 5 | — | — | — | 6 |

The deodorant efficacy of each formula was evaluated according to the following protocol:

0.5 g of formula was applied to the surface of an armpit. The armpits were washed with toiletry soap and then rinsed and dried (towel) before applying the product. One armpit was not treated and served as a reference for the evaluation.

After 24 hours, evaluations by direct "sniff test" of the intensity of the odour under the armpits were performed after application of a test composition and compared with the intensity of the odour under the untreated armpit.

The deodorant efficacy was evaluated according to the following two criteria:

The intensity of the odour on a scale from 1 to 10. 1 represents an imperceptible intensity and 10 represents an odour equivalent to that of the untreated armpit. The lower the value, the weaker the odour.

The hedonic value on a scale from 1 to 10. 1 represents an odour that is as unpleasant as that under the untreated armpit and 10 represents an extremely pleasant odour. The higher the value, the more the unpleasantness decreases.

Results

| Formula | Odour intensity | Hedonic value |
|---|---|---|
| Formula A (comparative) | 9 | 3 |
| Formula B (comparative) | 6 | 4 |
| Formula C (invention) | 2 | 6 |
| Formula D (invention) | 4 | 4 |

The results show that compositions C and D according to the invention make it possible to reduce efficiently the intensity of the odour. Composition C also gives a more pleasant odour.

Example 6

Anhydrous Deodorant Stick

| Ingredients (INCI name) | Amounts (weight %) |
|---|---|
| Cyclopentasiloxane (DC 245 ® - Dow Corning) | 38 |
| PPG-14 Butyl ether (Ucon fluid AP ® Amerchol) | 10 |

-continued

| Ingredients (INCI name) | Amounts (weight %) |
|---|---|
| Hydrogenated castor oil (Cutina HR ® - Cognis) | 4 |
| Stearyl alcohol (Lorol C18 ® - Cognis) | 14 |
| PEG-8 distearate (Stearineries Dubois) | 2 |
| C12-15 alkyl benzoate (Finsolv TN ® - Witco) | 15 |
| Siliceous material according to one of Examples 1 to 6 | 17 |
| Total | 100 |

Procedure:

The cyclopentasiloxane was heated to 65° C. The other ingredients were added (one by one), while keeping the temperature at 65-70° C. The whole was homogenized (transparent solution) for 15 minutes. The particles of siliceous material were added. The product was cooled to about 55° C. (a few degrees above the thickening point of the mixture) and poured into sticks. The sticks were placed at 4° C. for 30 minutes.

The composition applied to the armpits reduces the odour caused by perspiration.

Example 7

Deodorant Emulsion (Roll-on)

| Phase | Ingredients (INCI name) | Amounts (weight %) |
|---|---|---|
| A | Siliceous material according to one of Examples 1 to 6 | 10 |
| B | Steareth-21 (Brij 721 ® - ICI) | 2 |
| | Steareth-2 (Brij 72 ® - ICI) | 2 |
| | PPG-15 stearyl ether (Arlamol E ® - ICI) | 1.5 |
| | Cyclopentasiloxane (DC 245 ® - Dow Corning) | 3.5 |
| C | Water | qs for 100 |

Procedure:

Phases (B) and (C) were separately heated to 70° C. Phases (B) and (C) were mixed together with a Turrax blender for 5 minutes, and the mixture was then cooled to 55° C. with paddle stirring. Phase A was then added slowly with stirring. The mixture was homogenized for 1 to 3 minutes. The mixture was cooled to 35° C. with stirring. The composition applied to the armpits reduces the odour caused by perspiration.

Example 8

Deodorant and Antiperspirant Emulsion (Roll-on)

| Phase | Ingredients (INCI name) | Amounts (weight %) |
|---|---|---|
| A | Aluminium chlorhydrate (50% solution) (Chlorhydrol ® 50% - USP) | 35 |
|   | Siliceous material according to one of Examples 1 to 6 | 6 |
| B | Steareth-21 (Brij 721 ® - ICI) | 2 |
|   | Steareth-2 (Brij 72 ® - ICI) | 2 |
|   | PPG-15 stearyl ether (Arlamol E ® - ICI) | 1.5 |
|   | Cyclopentasiloxane (DC 245 ® - Dow Corning) | 3.5 |
| C | Water | qs for 100 |

Procedure:

Phases (B) and (C) were separately heated to 70° C. Phases (B) and (C) were mixed together with a Turrax blender for 5 minutes, and the mixture was then cooled to 55° C. with paddle stirring. Phase A was then added slowly with stirring. The mixture was homogenized for 1 to 3 minutes. The mixture was cooled to 35° C. with stirring.

The composition applied to the armpits reduces the odour caused by perspiration.

Example 9

Deodorant Paste

| Ingredients (INCI name) | Amounts (weight %) |
|---|---|
| Triethyl citrate (Citroflex 2 ® - Reilly Chemicals) | 7 |
| Isopropyl palmitate (Cognis) | 6 |
| Siliceous material according to one of Examples 1 to 6 | 17.5 |
| Cyclomethicone (Dow Corning 245 ® Fluid) | 60.5 |
| Cyclopentasiloxane (and) Dimethiconol (Dow Corning 1501 Fluid ®) | 9 |

Procedure:

The particles of siliceous material were dispersed in the mixture of the other starting materials using a paddle. A homogeneous paste was obtained.

The composition applied to the armpits reduces the odour caused by perspiration.

Example 10

Aerosol

| Phase | Ingredients (INCI name) | Amounts (weight %) |
|---|---|---|
| A | Triethyl citrate (Citroflex 2 ® - Reilly Chemicals) | 1.05 |

-continued

| Phase | Ingredients (INCI name) | Amounts (weight %) |
|---|---|---|
|   | Stearalkonium bentonite | 0.23 |
|   | Isopropyl palmitate (Cognis) | 0.9 |
|   | Hydrophobic modified silica according to one of Examples 1 to 6 | 2.625 |
|   | Cyclomethicone (Dow Corning 245 Fluid ®) | 9.075 |
|   | Cyclopentasiloxane (and) Dimethiconol (Dow Corning 1501 Fluid ®) | 1.35 |
| B | Isobutane | 85 |

Procedure:

The particles of siliceous material were dispersed in the mixture of the other starting materials constituting phase A, using a paddle. The mixture was pressurized with isobutane in an aerosol can.

The composition applied to the armpits reduces the odour caused by perspiration.

The invention claimed is:

1. A cosmetic process for treating human body odour and optionally human perspiration, which comprises applying to human keratin materials a siliceous material that may be obtained by hydrolysis and condensation, in the presence of water, of at least one tetraalkoxysilane of formula (I) below:

$$Si(OR_2)_4 \quad (I)$$

and of an alkyltrialkoxysilane of formula (II) below:

$$R_1Si(OR_2)_3 \quad (II)$$

in which:
 $R_1$ denotes a linear or branched $C_7$ to $C_{20}$ alkyl group, optionally interrupted in its chain with an O or S atom or with an NH group or a carbonyl group (CO),
 $R_2$ denotes a linear or branched $C_1$-$C_4$ alkyl group.

2. The cosmetic process according to claim 1, in which the said siliceous material is present in a composition comprising a cosmetically acceptable medium.

3. The cosmetic process according to claim 1, in which $R_1$ represents a $C_8$ to $C_{18}$ alkyl group.

4. The cosmetic process according to claim 1, in which $R_2$ represents a linear alkyl group comprising from 1 to 4 carbon.

5. The cosmetic process according to claim 1, in which compound (I) is chosen from tetraethoxysilane (TEOS) and tetramethoxysilane (TMOS).

6. The cosmetic process according to claim 1, in which compound (II) is chosen from n-octyltrimethoxysilane, n-dodecyltrimethoxysilane, n-octadecyltrimethoxysilane, n-octyltriethoxysilane, n-dodecyltriethoxysilane and n-octadecyltriethoxysilane, and mixtures thereof.

7. The cosmetic process according to claim 6, in which compound (II) is chosen from:
 n-dodecyltriethoxysilane
 n-octadecyltriethoxysilane
 n-octyltriethoxysilane.

8. The cosmetic process according to claim 1, in which the siliceous material may be obtained by hydrolysis and condensation, in the presence of water, of at least one tetraalkoxysilane of formula (I), of an alkyltrialkoxysilane of formula (II) and of at least one aminoalkyltrialkoxysilane of formula (III) below:

$$R_3Si(OR_4)_3 \quad (III)$$

in which:
  R₃ denotes a linear or branched, saturated or unsaturated C₁-C₆ hydrocarbon-based group or a cyclic C₃-C₅ hydrocarbon-based group, or denotes a C₆-C₉ aryl or C₆-C₉ aryloxy group, the said radicals being substituted with an amino group NH₂ or NHR with R denoting a C₁-C₄ alkyl group,
  R₄ denotes a linear or branched C₁-C₄ alkyl group.

9. The cosmetic process according to claim 8, in which R₃ represents a C₂-C₄ hydrocarbon-based group substituted with an amino group NH₂ or NHR with R denoting a linear or branched C₁-C₄ alkyl group.

10. The cosmetic process according to claim 8, in which R₄ represents an ethyl group.

11. The cosmetic process according to claim 8, in which the compound of formula (III) is chosen from 3-aminopropyltriethoxysilane (APTES), 3-aminoethyltriethoxysilane (AETES), 3-aminopropylmethyldiethoxysilane, N-(2-aminoethyl)-3-aminopropyltriethoxysilane, 3-(m-aminophenoxy)propyltrimethoxysilane, p-aminophenyltrimethoxysilane and N-(2-aminoethylaminomethyl)phenethyltrimethoxysilane.

12. The cosmetic process according to claim 11, in which compound (III) is 3-aminopropyltriethoxysilane (APTES).

13. The cosmetic process according to claim 1, in which compounds (I) and (II) are used in a compound (I)/compound (II) weight ratio ranging from 0.9 to 100.

14. The cosmetic process according to claim 8, in which compounds (I) and (III) are used in a compound (I)/compound (III) weight ratio ranging from 0.9 to 100.

15. The cosmetic process according to claim 1, in which R₁ represents an alkyl group chosen from n-octyl, n-decyl, n-dodecyl, n-tetradecyl, n-hexadecyl and n-octadecyl.

16. The cosmetic process according to claim 2, in which R₁ represents a C₈ to C₁₈ alkyl group.

17. The cosmetic process according to claim 1, in which R₂ represents an ethyl group.

18. The cosmetic process according to claim 3, in which R₂ represents a linear alkyl group comprising from 1 to 4 carbon atoms.

19. The cosmetic process according to claim 1, which comprises applying said siliceous material to underarms.

* * * * *